US005610149A

United States Patent [19]
Burrows et al.

[11] Patent Number: 5,610,149
[45] Date of Patent: Mar. 11, 1997

[54] STEROIDAL POLYAMINES

[75] Inventors: Cynthia J. Burrows, Salt Lake City, Utah; Hsing-Pang Hsieh, Taipei, Taiwan

[73] Assignee: The Research Foundation of State University of New York, Albany, N.Y.

[21] Appl. No.: 439,808

[22] Filed: May 12, 1995

[51] Int. Cl.$^6$ .......................... A61K 31/575; C07J 9/00; C07J 41/00
[52] U.S. Cl. ........................... 514/169; 552/509; 552/521
[58] Field of Search .............................. 552/509, 521; 514/169

[56] References Cited

PUBLICATIONS

H. P. Hsieh, "Synthesis of Novel Steroidal Polyamines and Structural Effects in DNA–Polyamine Binding", pp. 23–140, State University of New York at Stony Brook, submitted to committee Dec. 1993, indexed and shelved in library, May 12, 1994.
H–P. Hsieh, et al., "Structural Effects in Novel Steroidal Polyamine — DNA Binding", *J. Am. Chem. Soc.* 1994, 116: 12077–12078.
N. Schmid, et al., "Location of Spermine and Other Polyamines on DNA As Revealed by Photoaffinity Cleavage with Polyaminobenzenediazonium Salts," *Biochemistry* 1991, 30: 4357–4361.
K. D. Stewart, "The Effect of Structural Changes in a Polyamine Backbone on its DNA — Binding Properties", *Biochem. Biophys. Res. Commun.* 1988, 152: 1441–1446.
K. D. Stewart et al., "Survey of the DNA Binding Properties of Natural and Synthetic Polyamino Compounds," *J. Phys. Org. Chem.* 1992, 5:461–466.
H. R. Mahler et al., "Interaction of Steroidal Diamines With DNA and Polynucleotides," *Ann. N.Y. Acad. Sci.* 1970, 71: 783–800.
C. Zimmer et al., "Nonintercalating DNA — Binding Ligands: Specificity Of the Interaction and Their Use As Tools In Biophysical, Biochemical and Biological Investigations of the Genetic Material," *Prog. Biophys. Mol. Biol.* 1986, 47: 31–112.
J. M. Saucier, "Physicochemical Studies on the Interaction of Irehdiamine A With Bihelical DNA," *Biochemistry* 1977, 16: 5879–5889.
D. J. Patel et al., "Steroid Diamine — Nucleic Acid Interactions: Partial Insertion of Dipyrandium Between Unstacked Base Pairs of the Poly (dA –dT) Duplex in Solution," *Proc. Natl. Acad. Sci. U.S.A.* 1979, 76: 22–28.
X. Hui, et al., "Modelling Basic Features of Specificity in the Binding of a Dicationic Steroid Diamine to Double–Stranded Oligonucleotides," *Nucleic Acids Res.* 1989 17:4177–4187.
K. S. Moore, "Squalmine: An Aminosterol Antibiotic From the Shark," *Proc. Natl. Acad. Sci. USA* 1993, 90: 1354–1358.
C. J. Burrows, et al., "Synthesis and Conformational Studies of a New Host System Based on Cholic Acid", *J. Inclusion Phenom.* 1987, 5: 117–121.

J. F. Kinneary, et al., "Progress Toward Artificial Metalloenzymes: New Ligands for Transition Metal Ions and Neutral Molecules," *J. Inclusion Phenom.* 1989, 7:155–168.
A. P. Davis, "Cholophanes et al.; Steroids as Structural Components in Molecular Engineering," *Chem. Soc. Rev.* 1993, 22:243–253.
A. P. Davies et al., "Stereocontrolled Synthesis of Cholic Acid Derivatives With N–Protected 7B–and/or 12B — Amino Substituents," *Tetrahedron Lett.* 1992, 33: 5111–5112.
A. A. Malik and C. M. Shorts, "Selective Reduction of the Formulated Bile Acids to the Corresponding Formulated Bile Alcohols Analogs," *Org. Prep. Proced. Int.* 1987, 19: 1–7.
Y. Satoh, "Basic Bile Acids V On the Synthesis and Properties of Basic Bile Acids and Their Derivatives," *Bull. Chem. Soc. Jpn.* 1965, 38: 1581–1585.

(List continued on next page.)

*Primary Examiner*—Kimberly J. Prior
*Attorney, Agent, or Firm*—Hoffmann & Baron

[57] ABSTRACT

New steroidal polyamines have the structure of formula I or formula II:

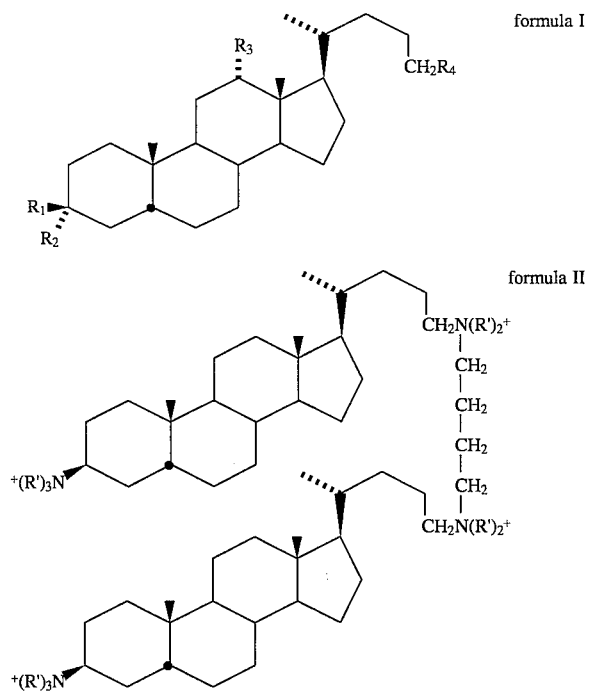

wherein
  $R_1$ and $R_2$ are independently $N(R')_3^+$ or H in the α- or β- position except both $R_1$ and $R_2$ are not H;
  $R_3$ is $N(R')_3^+$ in the α- position or hydrogen
  $R_4$ is OH, $N(R')_3$, or $NHC(NH_2)NH_2^+$
  R' is hydrogen, alkyl of one to four carbons, aralkyl, or combinations thereof.

10 Claims, 1 Drawing Sheet

OTHER PUBLICATIONS

J. P. Guthrie, et al., "The Synthesis of 17B-(4(5)imidazolyl)-5∝-androstane-3B, 11B-diamine: a Water Soluble Steroid With a Potentially Catalytic Substituent," *Can. J. Chem* 1972 50: 3993–3997.

J. P. Guthrie et al., "A Water Soluble Dimeric Steroid With Catalytic Properties Rate Enhancement From Hydrophobic Binding," *Can. J. Chem.* 1986, 64: 2456 –2469.

P. Rollin and M. C. Viaud, "Zinc Azide Mediated Mitsunobu Substitution An Expedient Method For the One–Pat Azidation of Alcohols," *Synthesis* 1990, 130–132.

H. Loibner et al., "Reaktionen Mit Phosphor — Organischen Verbindugen. XLII [1]. Nucleophile Substitutionen an Hydroxysteroiden mit Hilfe von Triphenylphosphan/Azodicarbonsäure ester," *Helv. Chim. Acta* 1977, 60: 417–425.

K. Kim et al., "Monsubstituted Guanidines From Primary Amines and Aminoiminomethanesulfonic Acid", *Tetrahedron Lett.* 1988, 29, 3183–3186.

B. F. Cain et al., "Potential Antitumor Agents 28 Deoxyribonucleic Acid Polyintercalating Agents," *J. Med. Chem.* 1978, 21:658–668.

H. J. Schneider et al., "Interactions Between Acyclic and Cyclic Peralkylammonium Compounds and DNA," *Angew. Chem. Int. Ed. Engl.* 1992, 31:1207–1208.

J. E. Morgan et al., "Association Constants For The Interaction of Double–Stranded and Single–Stranded DNA With Spermine, Spermidine, Putrescine, Diaminopropane, $N^1$- and $N^8$ -Acetylspermidine, and Magnesium: Determination from Analysis of the Broadening of Thermal Denaturation Curves," *Arch. Biochem. Biophys.* 1986, 246: 225–232.

J. A. McClarin et al., "Structure of the DNA — Eco RI Endonuclease Recognition Complex at 3Å Resolution" *Science* 1986, 234: 1526–1541.

M. Gourévitch et al., "Model Studies in Relation to the Molecular Structure of Chromatin," *Biochimie* 1974, 56: 967–985.

M. I. Gourévitch et al., "Physicochemical Studies On The Interaction of $\Delta^5$–Dehydromalouetine With DNA. Further Evidence For the Partial Insertion of a Steroidal Diamine Into a DNA Double Helix," *Int. J. Biol. Macromol.* 1986, 8: 97–104.

H. R. Mahler et al., "Nucleic Acid Interactions VI Effects of Steroidal Diamines," *Nucleic Acid Interact.* 1966, 5: 2177–2192.

R. T. Blickenstaff, *Antitumor Steroids,* Academic Press, Inc., San Diego 1992, pp. 180–183.

STEROIDAL POLYAMINES

The invention was made with government support under National Science Foundation grant number CHE 9006684. The government has certain rights in the invention.

The invention relates to new steroidal polyamines having certain structural effects and DNA binding and their pharmaceutical effects as antibiotics and antineoplastics.

BACKGROUND OF THE INVENTION

Efforts to understand the interactions of drugs and toxins with DNA as well as the desire for new methods of DNA manipulation have spurred the design and synthesis of small molecules that bind in specific ways to DNA.

The biogenic polyamines (putrescine, spermidine, spermine) bind primarily in the minor groove and are thought to hydrogen bond with donor atoms on the edges of the base pairs rather than associating with the phosphate backbone.[1] Studies of simple aliphatic polyamines[2] suggest that the three- to four-carbon spacing between ammonium groups is nearly ideal for matching the spacing of base pairs along the minor groove ladder while ensuring full protonation of the amines at pH 7.

The naturally occurring steroidal diamines such as irehdiamine A, malouetine, dipyrandium, and chonemorphine bearing ammonium groups at C3 and C17 (or the adjacent carbon, C20) of the steroid are amphiphilic in nature, presenting a large hydrophobic group between the cationic extremities.[3] Their biophysical features include unwinding of superhelical DNA, increasing the duplex denaturation temperature, and altering of the UV and CD spectra of DNA while such biochemical functions as aiding in membrane permeability, ion transport, and DNA replication and multagenesis are also observed.[4] For dipyrandium, binding to DNA is proposed to occur in the minor groove in conjunction with 5'-d(TA) kinks.[5]

A lipospermine for gene transfer is marketed in Europe under the name transfectam (Prolabo).

The steroidal diamines, as well as the recently reported steroidal spermidine, squalamine, isolated from sharks, are of considerable interest as antibiotics.[6]

SUMMARY OF THE INVENTION

The invention relates to new synthetic steroidal polyamines in which the number and position of ammonium, amine or guanidinium groups can be varied.

The compounds of the invention have formula I or formula II:

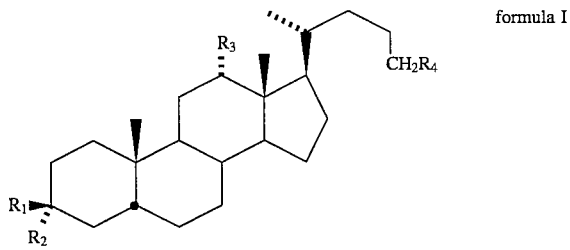

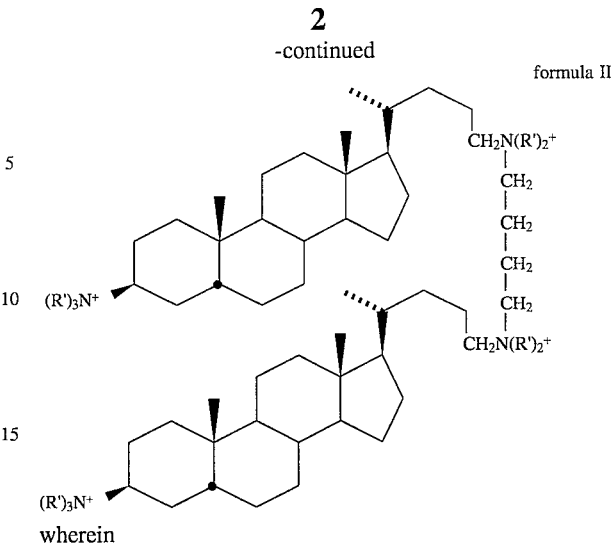

wherein $R_1$ and $R_2$ are independently $N(R')_3^+$ or H in the α- or β-position except that both $R_1$ and $R_2$ are not H;

$R_3$ is $N(R')_3^+$ in the α- position or H;

$R_4$ is OH, $N(R')_3^+$ or $NHC(NH_2)NH_2^+$;

R' is hydrogen, alkyl of one to four carbons, aralkyl or combinations thereof.

Preferred embodiments of formula I include compounds 1–6 which include the following:

1  $R_1$=H, $R_2$=$NH_3^+$, $R_3$=$NH_3^+$, $R_4$=CH
2  $R_1$=$NH_3^+$, $R_2$=H, $R_3$=$NH_3^+$, $R_4$=OH
3  $R_1$=H, $R_2$=$NH_3^+$, $R_3$=H, $R_4$=$NH_3^+$
4  $R_1$=$NH_3^+$, $R_2$=H, $R_3$=H, $R_4$=$NH_3^+$
5  $R_1$=$NH_3^+$, $R_2$=H, $R_3$=$NH_3^+$, $R_4$=$NH_3^+$
6  $R_1$=$NH_3^+$, $R_2$=H, $R_3$=H, $R_4$=$NHC(NH_2)NH_2^+$

A preferred embodiment of formula II includes compound 7:

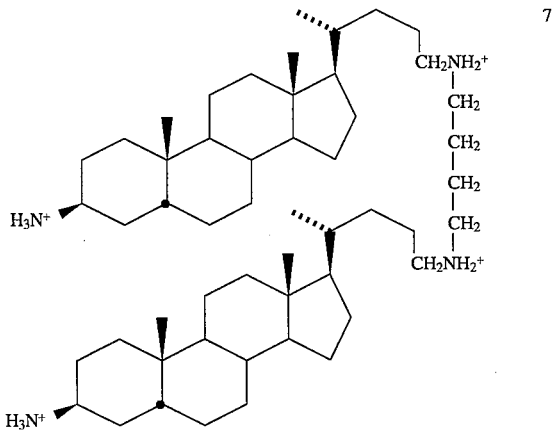

Advantageously, the compounds have good water solubility and membrane permeability. In addition, the compounds have the ability to bind DNA by one to three orders of magnitude better than simple aliphatic polyamines. Therefore, the compounds are good anti-sense oligonucleotide carriers.

The compounds are suitable for use in pharmacological compositions as antibiotics and antitumor agents and for use in gene transfer.

DETAILED DESCRIPTION OF THE INVENTION

Figure 1:
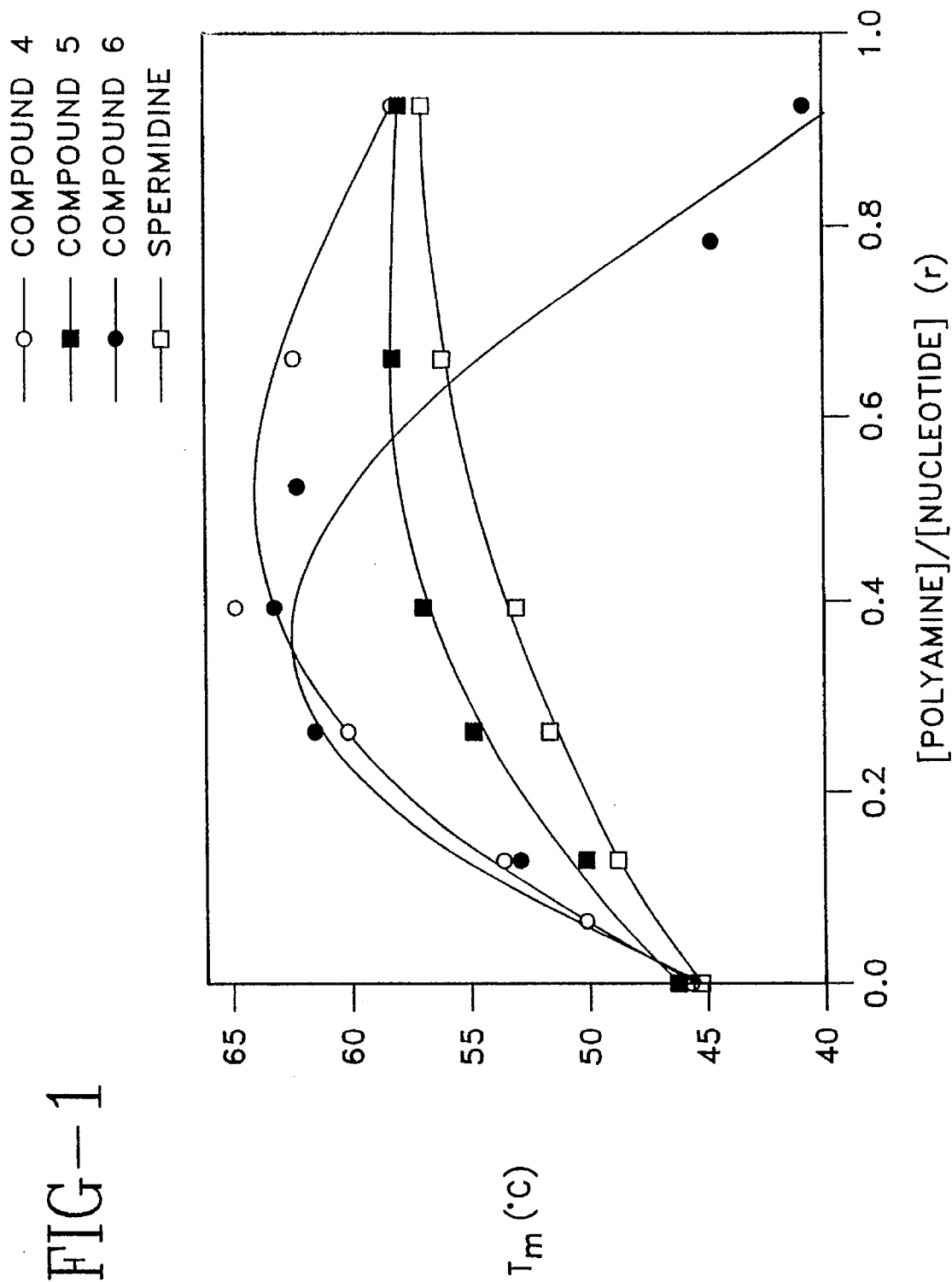
FIG. 1 is a graph showing the effect of polyamine binding on $T_m$ of poly d(AT). $T_m$ values were measured by monitoring the 260 nm absorbance using 0.025 SHE buffer (23 mM NaCl, 2 mM HEPES, 0.5 mM EDTA, pH 7.0). Error limits are: ±1°. $T_m$ is melting temperature.

Bile acids such as cholic acid and its derivatives offer a convenient framework for construction of the instant species.[7] Accordingly, we prepared the steroidal diamines 1–4, triamine 5, amino-guanidinium 6, and the steroid dimer 7, a tetraamine, and examined their binding to DNA.

The polyamines were synthesized from either deoxycholic acid or lithocholic acid, depending on whether or not functionality was desired at C12.[8] Both acids were first reduced to the corresponding C24 alcohols using $BH_3$/THF.[9] Both the 3α-OH and the 12α-OH groups could be converted to α-$NH_2$ groups by oxidation with pyridinium dichromate, formation of the oxime, and reduction with Na/n-propanol.[10] The 3β-$NH_2$ group was introduced by conversion of the 3α-OH to the corresponding 3β-azide under Mitsunobu conditions ($HN_3$ or $ZN(N_3)_2$, $PPh_3$, DEAD)[11] followed by reduction of the azide with either catalytic hydrogenation or $LiAlH_4$. This latter procedure was also used to introduce the C24 amine, which could be subsequently converted to a guanidinium group using aminoiminomethanesulfonic acid.[12] Finally, the dimeric steroid 7 was synthesized by a 2:1 coupling of lithocholic acid with 1,4-diaminobutane via the N-hydroxysuccinimide ester, the Mitsunobu method to introduce the amine at C3, and reduction of the amides with $BH_3$/THF. Subsequently, all of the free steroidal amines were converted to polyammonium salts by treating with ethereal HCl, and the salts were used in DNA binding studies. Variations on these synthetic procedures were used, including protection and deprotection at various sites depending upon the desired target molecule.[13] All new compounds were purified by column chromatography and successfully characterized by $^1H$ and $^{13}C$ NMR, IR, FAB-MS, and elemental analysis.

The compounds can be further reacted by methods known in the art, e.g., by treatment with alkyl or aralkyl halides (such as methyl iodide), to substitute alkyl or aralkyl groups for one, two or three hydrogens on the primary amine moieties yielding secondary, tertiary or quaternary groups. Alkyl includes one to four carbons and is preferably methyl. Aralkyl is preferably benzyl.

DNA binding studies were carried out using calf thymus DNA (CT-DNA) as well as poly d(AT) and poly d(GC). The experimental method employed was an ethidium displacement assay following previously reported literature.[2,14] The $C_{50}$ value was determined as the concentration of the steroidal polyamine leading to a 50% reduction in the fluorescence intensity of bound ethidium (excitation at 547 nm, emission at 595 nm) under 0.01 SHE buffer conditions (8 mM NaCl, 2 mM HEPES, 0.05 mM EDTA, (ethidium)= 1.26 μM, (DNA base pairs)=1.31 μM, pH 7, 25° C.). Although $C_{50}$ values cannot be directly translated into binding constants because the mode and stoichiometry of binding ethidium and by steroidal polyamines is not the same, they nevertheless offer a convenient qualitative means of comparing structural effects of the polyamine on DNA binding. As a point of reference, independent studies estimate a dissociation constant, $K_d$, in the range 0.1–1.0 μM for spermine binding to DNA[15] while studies in our laboratory and others place the $C_{50}$ value at about 1 μM.[2a,14b]

A comparison of $C_{50}$ values for polyamines and DNA is provided in Table 1.

TABLE 1

Polyamine binding to poly d(AT), calf thymus DNA and poly d(GC).

| example | polyamine | $C_{50}{}^a$ (μM) poly d(AT) | CT-DNA | poly d(GC) |
|---|---|---|---|---|
| 1 | putrescine $H_3N^+(CH_2)_4NH_3^+$ | | (1700[b]) | |
| 2 | spermidine $H_3N^+(CH_2)_4NH_2^+(CH_2)_3NH_3^+$ | | (27[b]) | |
| 3 | spermine $H_3N^+(CH_2)_3NH_2^+(CH_2)_4NH_2^+(CH_2)_3NH_3^+$ | 2.7 (2.8[b]) | 1.0 (1.6[b], 1.2[c]) | 1.1 (1.2[b]) |
| 4 | 3α,12α-diamine (1) | 280 | 290 | 380 |
| 5 | 3β,12α-diamine (2) | 34 | 29 | 42 |
| 6 | 3α,24-diamine (3) | 8 | 11 | 18 |
| 7 | 3β,24-diamine (4) | 10 | 16 | 24 |
| 8 | 3β,12α,24-triamine (5) | 10 | 14 | 17 |
| 9 | 3β-amine,24-guanidine (6) | 2.5 | 4.7 | 6.0 |
| 10 | 3β,3β',24,24'-tetraamine (7) | 0.16 | 0.24 | 0.18 |

[a]Polyamine concentration necessary to displace 50% of DNA-bound ethidium under the conditions: [DNA-bp]$_0$ = 1.31 μM, [ethidium]$_0$ = 1.26 μM, 0.01 SHE buffer (8 mM NaCl, 0.05 mM EDTA, 2 mM HEPES, pH 7.0). Values reported are the average of at least 3 independent experiments.
[b]Reference 2.
[c]Reference 14b.

For the series putrescine-spermidine-spermine, it is seen that the successive addition of an ammonium group on a $C_3$–$C_4$ chain provides a 30–60-fold increase in DNA binding (i.e., 30–60-fold decrease in $C_{50}$). The new steroidal polyamines show the following binding characteristics: (i) All of the steroidal diamines show substantially stronger DNA binding than the simple diamine putrescine. This is likely due to a substantial hydrophobic contribution to binding. (ii) Diamines 1 and 2 (examples 4 and 5) differ only in the configuration of the ammonium group at C3, yet their binding abilities differ by an order of magnitude. The same sensitivity to stereochemistry at C3 is not observed when the second ammonium group is placed on the flexible hydrocarbon chain at C24 rather than in a rigidly defined site such as at C12. (Compare examples 6 and 7). (iii) Binding of the steroidal triamine 5 (example 8) to DNA gives $C_{50}$ values that are nearly identical to those of the two related diamines 2 and 4. One interpretation is that the triamine binds via only two out of three of the ammonium groups. Alternatively, the expected gain in binding energy of a third ammonium group may be compromised by the loss of a large hydrophobic area when C12 is aminated in addition to C3 and C24. (iv) Conversion of the 24-amino group of diamine 4 to a guanidinium group results in a 4-fold enhancement in binding (compare examples 7 and 9). This is likely due to the greater hydrogen-bonding ability of guanidinium groups as demonstrated in a number of protein-DNA complexes in which arginine residues play a major role in DNA recognition.[16] (v) Tetraamine 7 binds to DNA about 2 orders of magnitude better than does the triamine, and nearly an order of magnitude better than does spermine. This again supports the notion that inclusion of large hydrophobic regions such as a steroid nucleus aids substantially in DNA binding.

Additional insight concerning the role of hydrophobicity was gained from the thermal denaturation studies of poly d(AT) as a function of added polyamine (FIG. 1). Spermidine binding to poly d(AT) results in stabilization of duplex DNA observed as an increase in $T_m$. This effect saturates at a (polyamine): (nucleotide) ratio, r, of about 0.5. Diamine 4, however, initially stabilizes the duplex and then destabilizes it at higher r values. The same behavior has been observed for other steroidal diamines, notably irehdiamine A.[17] The guanidinium-appended steroid 6 displayed this curvature even more markedly in the $T_m$ vs r study. In contrast, the steroidal triamine 5 behaved much more like the simple triamine, spermidine, in $T_m$ studies suggesting that the binding mode of 5 may be more like the biogenic amines. Interruption of the hydrophobic region of the steroid by introduction of the 12α-amino group midway along the 14-carbon span between C3 and C24 makes 5 resemble spermidine as it binds to DNA. Interestingly, the complementary and opposite effect has already been seen when putrescine binding is compared to that of 1,12-diaminododecane. The chain-lengthened diamine demonstrates higher binding affinity as well as a bell-shaped $T_m$ vs r curve for poly d(AT) binding.[17a] Consistent with this analysis, the dications 4 and 6 caused respectively 9% and 17% hyperchromicity of poly d(AT) at 260 nm whereas 5 as well as spermine and spermidine showed no change in absorbance.[18] Hyperchromicity is often associated with a disruption in base stacking related to partial intercalation.[4a,17b,c]

This new series of steroidal polyamines demonstrates that DNA binding can be tailored by the stereo and regiochemistry of appended ammonium groups in addition to the total number of ammoniums and the hydrophobic contribution of the steroid nucleus. At least two different binding modes are observed, one resembling the biogenic amines such as spermidine and the other more characteristic of the natural product steroidal diamines. The bile acid framework offers a convenient entry into such molecules and will aid in correlation of the structure of steroidal polyamines to their biological activity.

Accordingly, new steroidal polyamines containing ammonium groups at the 3α, 12α-, 3β, 12α-, 3α, 24-, 3β, 24-, and 3β, 12α, 24- positions, as well as one containing a 3β-ammonium and 24-guanidinium and another consisting of 2 units of the 3β, 24-diammonium linked by a $C_4$ chain have been synthesized from deoxycholanol and lithocholanol.

These compounds are 1. 3α,12α-diamino-5β-cholan-24-ol dihydrohalide
2. 3β,12α-diamino-5β-cholan-24-ol dihydrohalide
3. 5β-cholane-3α,24-diamine dihydrohalide
4. 5β-cholane-3β,24-diamine dihydrohalide
5. 5β-cholane-3β,12α,24-triamine trihydrohalide
6. 3β-amino-24-guanidino-5β-cholane dihydrohalide
7. N,N-bis(3β-amino-5β-cholan-24-yl)1,4-diaminobutane tetrahydrohalide or salts thereof.

DNA binding studies using calf thymus DNA, poly d(GC) and poly d(AT) confirm that the DNA affinities of the polyamines are most dependent upon charge, and secondarily dependent upon the stereochemical disposition of the ammonium groups. A direct comparison of an ammonium group and a guanidinium group on the steroid showed a slight preference for guanidinium binding to DNA. Consistently stronger binding to poly d(AT) compared to poly d(GC) was observed.

We were able to control solubility by the number of ammonium and hydroxyl groups on the steroid. At the same time, the steroid framework provides good membrane permeability.

While it is not intended to be bound by any particular theory, it is believed that steroidal polyamine conjugates with antisense oligonucleotides show improved cellular uptake because of the charge neutralization by the polyammonium group and the membrane affinity of the steroid group.

The compounds have structural similarity and biological activity similarity to naturally occurring biogenic polyamines irehdiamine A, dipyrandium and squalamine. In addition, the compounds may be used for coupling to anti-sense oligonucleotides or other drugs for enhanced membrane permeability.

The compounds of the invention have been found to possess valuable pharmacological properties, e.g., as antibiotics and antineoplastics. They can be used as antibacterials, antifungals, antiseptics, and antitumor agents in human and veterinary medicine. The pharmaceutic effects can be demonstrated by known screening methods used in the pharmaceutical industry. Antitumor effects are described by R. T. Blickenstaff, *Antitumor Steroids*, Academic Press, San Diego 1992. Antibiotic steroid effects are described, e.g., by K. S. Moore et al., "Squalamine: An Aminosterol Antibiotic From the Shark", Proc. Natl. Acad. Sci. USA, 90, 1354–1358, 1993.

The compounds can be employed in admixture with conventional excipients, i.e., pharmaceutically acceptable carriers and other active or inactive pharmaceutical ingredients. "Acceptable" means compatible with the other ingredients of the formulation and non-injurious to the subject or material being treated. These carriers include those well known in the art as suitable for oral, rectal, nasal, topical, buccal, sublinguinal, vaginal, transdermal, subcutaneous, intradermal, intramuscular, intravenous or other parenteral administration, and in controlled, sustained or direct release form.

In general, a suitable dose for mammals, including humans is in the range of about 5 µg to 500 mg per day. Although higher and lower amounts may be used depending on the severity of the infection.

It will be appreciated that the actual preferred amounts of active compound in a specific case will vary according to the specific compound being utilized, the particular compositions formulated, the mode of application, the particular sites and the organism being treated. Dosages for a given host can be determined using conventional considerations, e.g., by customary comparison of the different activities of the subject compounds and of a known agent, e.g., by means of an appropriate conventional pharmacological protocol.

Advantageously for use in physiological systems, the compounds are water soluble, active and non-toxic at concentrations sufficient for effective killing or inhibition of the microorganisms or tumor cells.

Example 11: The compounds were screened for antibiotic activity and good antibiotic activity was found against both gram positive and gram negative bacteria and fungi.

BIBLIOGRAPHY (1) Schmid, N.; Behr, J. P. *Biochemistry* 1991, 30, 4357–4361.

(2) (a) Stewart, K. D. *Biochem, Biophys. Res. Commun.* 1988, 152, 1441–1446. (b) Stewart, K. D.; Gray, T. A. *J. Phys. Org. Chem.* 1992, 5, 461–466.

(3) (a) Mahler, H. R.; Green, G. *Ann. N.Y. Acad. Sci.* 1970, 71, 783–800. (b) Zimmer, C.; Wahmert, U. *Prog. Biophys. Mol. Biol.* 1986, 47, 31–112.

(4) (a) Saucier, J-M. *Biochemistry* 1977, 16, 5879–5889. (b) Sliver, S.; Wendt, L.; Bhattachargya, P. In *Antibiotics III. Mechanisms of Action of Antimicrobial and Antitumor Agents*; Corcoran, J. W., Hahn, F. E., Eds; Springer-Verlag: Heidelberg 1975; pp 614–622.

(5) (a) Patel, D. J. Canuel, L. L. *Proc. Natl. Acad. Sci. U.S.A.* 1979, 76, 22–28. (b) Hui, X.; Gresh, N.; Pullman, B. *Nucleic Acids Res.* 1989, 17, 4177–4187.

(6) Moore, K. S.; Wehrli, S.; Roder, H.; Rogers, M.; Forrest, J. N., Jr.; McCrimmon, D.; Zasloff, M. *Proc. Natl. Acad. Sci. U.S.A.* 1993, 90, 1354–1358.

(7) (a) Burrows, C. J.; Sauter, R. A. *J. Inclusion Phenom.* 1987, 5, 117–121. (b) Kinneary, J. F.; Roy, R. M.; Albert, J. S.; Yoon, H.; Wagler, T. R.; Shen L.; Burrows, C. J. *J. Inclusion Phenom.* 1989, 7, 155–168. (c) Davis, A. P. *Chem. Soc. Rev.* 1993, 22, 243–253.

(8) For an alternative approach to amination of steroids, see: Davis, A. P.; Orchard, M. G. *Tetrahedron Lett.* 1992, 33, 5111–5112.

(9) Sharts, C. M.; Malik, A. A. *Org. Prep. Proced. Int.* 1987, 19, 1–7.

(10) (a) Satoh, Y. *Bull. Chem. Soc. Jpn.* 1965, 38, 1581–1585. (b) Guthrie, J. P. *Can. J. Chem.* 1972, 50, 3993–3997. (c) Guthrie, J. P.; Cossar, J.; Dawson, B. A. *Can. J. Chem.* 1986, 64, 2456–2469.

(11) (a) Rollin, P.; Viaud, M. *Synthesis* 1990, 130–132. (b) Loibner, H.; Zbiral, E. *Helv. Chim. Acta* 1977, 60, 417–425.

(12) Kim, K.; Lin, Y.; Mosher, H. S. *Tetrahedron Lett.* 1988, 29, 3183–3186.

(13) Supplementary material is available for complete details of synthesis and characterization.

(14) (a) Cain, B. F.; Baguley, B. C.; Denny, W. A. *J. Med. Chem.* 1978, 21, 658–668. (b) Schneider, H-J; Blatter, T. *Angew. Chem., Int. Ed. Engl.* 1992, 31, 1207–1208.

(15) The $K_d$ value is highly dependant on medium, especially ($Na^+$). Morgan, J. E.; Blankenship, J. W.; Matthews, H. R. *Arch. Biochem. Biophys* 1986, 246, 225–232. See also ref. 2a.

(16) See, for example: McClarin, J. A.; Frederick, C. A.; Wang, B. C.; Greene, P.; Boyer, H. W.; Grable, J.; Rosenberg, J. M. *Science* 1986, 234, 1526–1541.

(17) (a) Gourévitch, M.; Puigdoménech, P.; Cavé, A.; Etienne, G.; Méry, J.; Parello, J. *Biochimie* 1974, 56, 967–985. (b) Gourévitch, M-I.; Puigdoménech, P. *Int. J. Biol. Macromol.* 1986, 8, 97–104. (c) Mahler, H. R.; Goutarel, R.; Khuong-Huu, Q.; Ho, M. T., *Nucleic Acid Interact.* 1966, 5, 2177–2192.

We claim:

1. A compound of formula I or formula II, or a salt thereof:

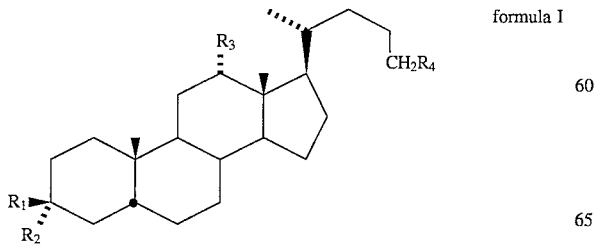

formula I

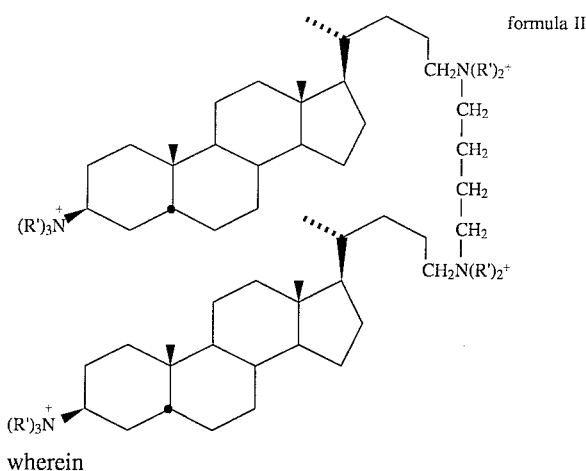

formula II wherein $R_1$ and $R_2$ are independently $N(R')_3^+$ or H in the α- or β-position except both $R_1$ and $R_2$ are not H;

$R_3$ is $N(R')_3^+$ in the α- position or hydrogen $R_4$ is OH, $N(R')_3^+$ or $NHC(NH_2)NH_2^+$ and R' is selected from the group consisting of hydrogen, alkyl of one to four carbons, aralkyl or combinations thereof.

2. A compound of formula I of claim 1 wherein $R_1$ is hydrogen, $R_2$ is ammonium, $R_3$ is ammonium and $R_4$ is hydroxyl.

3. A compound of formula I of claim 1 wherein $R_1$ is ammonium, $R_2$ is hydrogen, $R_3$ is ammonium and $R_4$ is hydroxyl.

4. A compound of formula I of claim 1 wherein $R_1$ is hydrogen, $R_2$ is ammonium, $R_3$ is hydrogen and $R_4$ is ammonium.

5. A compound of formula I of claim 1 wherein $R_1$ is ammonium, $R_2$ is hydrogen, $R_3$ is hydrogen and $R_4$ is ammonium.

6. A compound of formula I of claim 1 wherein $R_1$ is ammonium, $R_2$ is hydrogen, $R_3$ is ammonium and $R_4$ is ammonium.

7. A compound of formula I of claim 1 wherein $R_1$ is ammonium, $R_2$ is hydrogen, $R_3$ is hydrogen and $R_4$ is $NHC(NH_2)NH_2$.

8. A compound of formula II of claim 1 wherein R' is hydrogen.

9. The compound of claim 1 selected from the group consisting of 3α,12α-diamino-5β-cholan-24-ol dihydrohalide, 3β12α-diamino-5β-cholan-24-ol dihydrohalide, 5β-cholane-3α,24-diamine dihydrohalide, 5β-cholane-3β,24-diamine dihydrohalide, 5β-cholane-3β,12α,24-triamine trihydrohalide, 3β-amino-24-guanidino-5β-cholane dihydrohalide, N,N-bis(3β-amino-5β-cholan-24-yl)1,4-diaminobutane tetrahydrohalide, and salts thereof.

10. A pharmaceutical composition comprising at least one compound of claim 1 in admixture with a pharmaceutically acceptable carrier.

* * * * *